United States Patent [19]

Tangney

[11] Patent Number: 4,961,532

[45] Date of Patent: Oct. 9, 1990

[54] FRAGRANCE RELEASE DEVICE CONTAINING A HIGHLY ADSORPTIVE COPOLYMER

[75] Inventor: Kathryn R. Tangney, Midland, Mich.

[73] Assignee: Dow Corning Corporation, Midland, Mich.

[21] Appl. No.: 376,491

[22] Filed: Jul. 7, 1989

[51] Int. Cl.$^5$ .................................................. A61L 9/04
[52] U.S. Cl. ..................................................... 239/60
[58] Field of Search ........................ 239/34, 47, 55, 60; 261/DIG. 17; 422/4, 5, 291

[56] References Cited

U.S. PATENT DOCUMENTS

| | | |
|---|---|---|
| Re. 27,026 | 1/1971 | Alfrey et al. ........................ 260/2.5 |
| 2,239,628 | 4/1941 | Seki .................................. 239/44 X |
| 2,809,943 | 10/1957 | Pye et al. ............................ 260/2.1 |
| 3,418,262 | 12/1968 | Werotte et al. ..................... 260/2.2 |
| 3,509,078 | 4/1970 | Roubinek et al. .................. 260/2.5 |
| 3,627,708 | 12/1971 | Morse et al. ....................... 260/2.5 |
| 3,637,535 | 1/1972 | Corte et al. ........................ 260/2.1 |
| 3,767,600 | 10/1973 | Albright ............................. 260/2.2 |
| 3,989,649 | 11/1976 | Kailto et al. ....................... 260/2.1 |
| 4,208,309 | 6/1980 | Kraemer et al. ..................... 260/8 |
| 4,224,415 | 9/1980 | Meitzner et al. .................... 521/38 |
| 4,226,829 | 10/1980 | Mike ................................ 239/55 X |
| 4,509,682 | 4/1985 | Heiman et al. ..................... 239/60 |
| 4,534,509 | 8/1985 | Holzner ............................. 239/34 |
| 4,600,146 | 7/1986 | Ohno ................................. 239/6 |
| 4,661,327 | 4/1987 | Horton .............................. 423/7 |
| 4,690,825 | 9/1987 | Won .................................. 424/501 |
| 4,719,040 | 1/1988 | Traas ................................ 512/4 |
| 4,724,240 | 2/1988 | Abrutyn ............................ 514/847 |
| 4,747,539 | 5/1988 | Spector ............................. 239/47 |
| 4,764,362 | 8/1988 | Barchas ............................. 424/61 |
| 4,776,358 | 10/1988 | Korsk ............................... 132/321 |
| 4,793,555 | 12/1988 | Lee .................................. 239/6 |
| 4,806,360 | 2/1989 | Leong ............................... 424/487 |
| 4,813,976 | 3/1989 | Barchas ............................. 51/293 |
| 4,828,542 | 5/1989 | Hermann ............................ 604/3 |

FOREIGN PATENT DOCUMENTS

| | | |
|---|---|---|
| 1168157 | 5/1984 | Canada . |
| 61701 | 10/1982 | European Pat. Off. . |
| 0218891 | 4/1987 | European Pat. Off. . |
| 0218892 | 4/1987 | European Pat. Off. . |
| 0252463 | 1/1988 | European Pat. Off. . |
| 0306236 | 3/1989 | European Pat. Off. . |
| 2608533 | 9/1976 | Fed. Rep. of Germany . |
| 8801164 | 2/1988 | PCT Int'l Appl. . |
| 8702389 | 9/1987 | South Africa . |

Primary Examiner—Andres Kashnikow
Assistant Examiner—Kevin P. Weldon
Attorney, Agent, or Firm—Jim L. DeCesare

[57] ABSTRACT

A fragrance controlled release device including a container having at least two chambers, the two chambers being symmetrical and in the shape of an hourglass, a reduced and restricted channel for providing communication between the two chambers, the channel being of a diameter substantially less than the diameters of the two chambers, porous particulate carrier powder in one of the chambers, the one chamber being air impermeable and the other chamber being air permeable, and a fragrance contained and entrapped within the carrier powder.

6 Claims, 7 Drawing Sheets

2000X

1500X

1000 X

ORPM

⊢——⊣ 10 μm

1000 X

75 RPM

⊢——⊣ 10 μm

1000 X
150 RPM

|—————| 10 μm

1000 X
300 RPM

|———| 10 μm

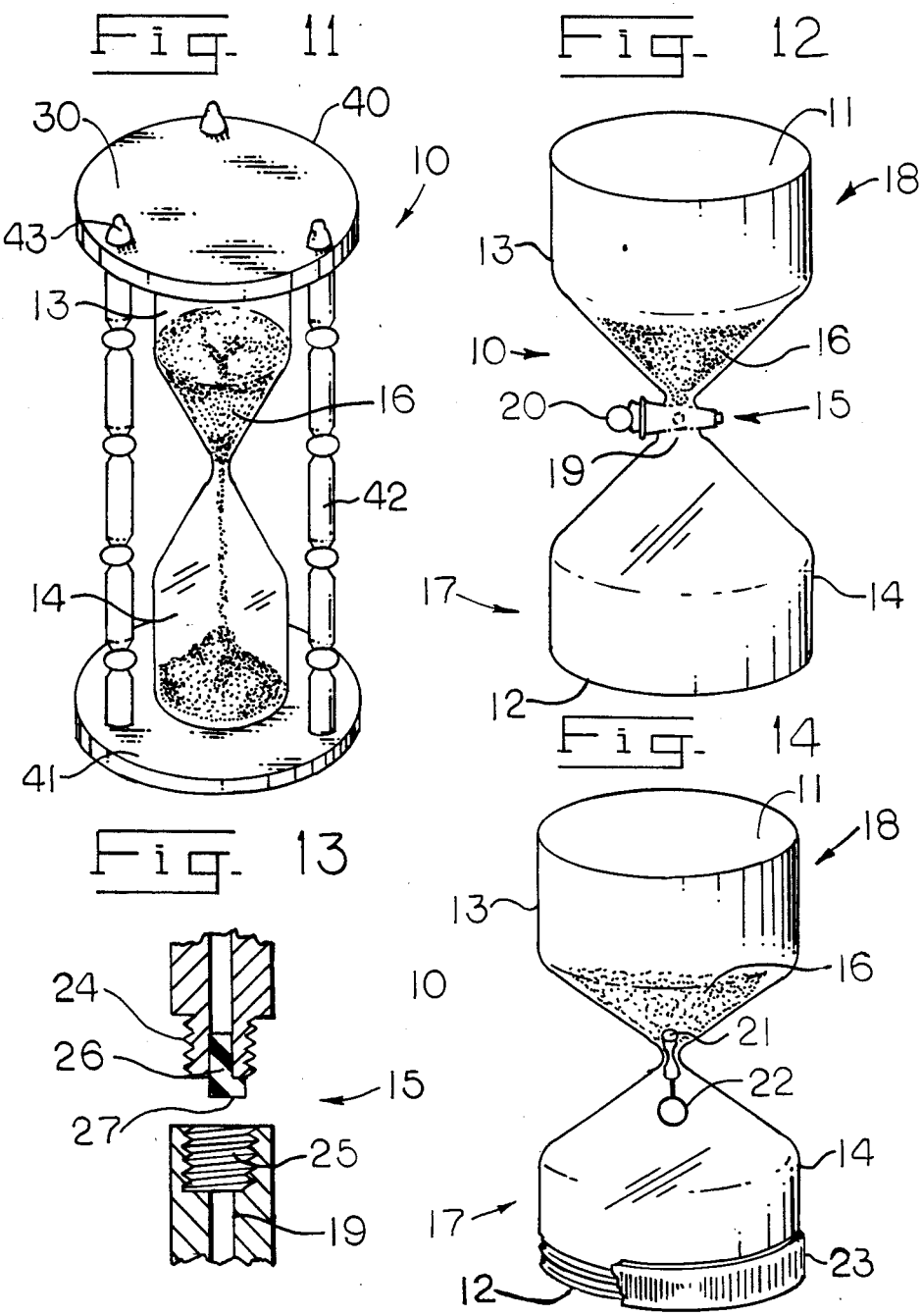

FRAGRANCE RELEASE DEVICE CONTAINING A HIGHLY ADSORPTIVE COPOLYMER

BACKGROUND OF THE INVENTION

This invention relates to a fragrance controlled release device for emitting pleasant aromas into the immediate environment. More particularly, the invention is directed to a device in the shape of an hourglass, and which includes a porous particulate carrier containing entrapped fragrance. The fragrance is released from the carrier when the hourglass is inverted.

Odor modification is the intentional change of one odor by the addition of another more acceptable odor. Air fresheners, perfumes, and industrial deodorants typify odor modifiers, in that they employ fragrance materials for odor control by altering a malodor to a more pleasant character or to an acceptable level. Among the most serious effects of malodors are coughing, headache, nausea, irritation of mucous membranes, and shortness of breath. The need for control of such effects is obvious in locations such as nursing homes, hospitals, restaurants, houses, automobiles, boats, and in the work-a-day environment. Malodors that must be combatted are human body odor, cigarette smoke, toilet odors, and the odor of cooking foods, for example. Generally, the control of body odor is by means of colognes and perfumes, whereas fragrance containing products are employed for industrial and household applications. The prior art is replete with delivery systems for fragrances, colognes, and perfumes. Exemplary systems for the application of fragrances and air fresheners locally or into the immediate environment are sprays, aerosols, sticks, wicks, liquid creams and lotions, atomizers, cellulosic and paper matrices. One method developed for timed or controlled release is by means of matrix devices in which a solute to be delivered is compounded into a matrix, generally a polymer such as cellulose esters, polyvinylchloride, polytetrafluoroethylene, polypropylene, polycarbonate, polyethylene, polystyrene, and nylon, and which may be in the form of a flat sheet The solute agent is then released from the matrix by diffusion, and the rate of release decreases with time and is not constant, and is typified by first order release kinetics. A relatively constant release rate, characterized by zero order release kinetics, can be achieved by means of depot or reservoir devices in which the rate controlling membrane encloses a cavity that contains the active solute ingredient. The reservoir provides substantially constant solute activity until the solute is exhausted by diffusion. However, the controlled release devices of the prior art suffer from the disadvantage that the duration of fragrance release is limited, often requiring many daily as well as many weekly applications in order to insure the activity of these products. In contrast, the present invention provides new delivery methods and improved controlled release devices for sustaining the release of fragrances, colognes, and perfumes.

In published unexamined European Pat. application No. 0186146A2, dated July 2, 1986, of Japan Liquid Crystal Co., Ltd., it is stated that the direct addition of perfume to a synthetic resin compound is not practical or effective because the perfume is volatile, liable to denature, and unstable to heat, so that it is difficult to mold a mixture of perfume and a synthetic resin into a desired shape. The patentee therefore forms an inclusion compound of a perfume in cyclodextrin, powders and dries the inclusion compound, and mixes the powder with the synthetic resin to form products. The patentee mentions silicone resin as a synthetic resin and the silicone resin is employed with the inclusion compound of cyclodextrin, liquid parafin, and benzotriazole, to produce semi-conductor substrates exhibiting rust preventative, mold-mildew proofing, or antifungal effects. In accordance with the present invention, however, improved and unexpected results are obtained contrary to such teachings and in the absence of the necessity of pre-forming a perfume into an inclusion composition for later formulation into a resin. In another published unexamined European Pat. application No. 0218891A2 dated Apr. 22, 1987, of Union Camp Corporation, a silicone rubber which is a cross-linked silicone elastomer of the type vulcanized at room temperature, is used in the construction of an elongated hollow cylindrical body member that includes a chamber containing about fifty grams of a volatile liquid fragrance that is intended to be diffused through the cylinder walls and into the atmosphere. A companion application No. 0218892A2 uses the same silicone rubber material but in the shape of a closure member for a glass container holding about fifty grams of volatile liquid fragrance which diffuses into the atmosphere through the silicone elastomer closure member. In U.S. Pat. No. 4,600,146, issued July 15, 1986, to Shin-Etsu Chemical Co., Ltd., a polymeric material such as an organopolysiloxane is formed into a capillary tube that is wire reinforced and filled with fragrance material which diffuses into the atmosphere through the walls of the tube. While these devices utilize silicone materials for diffusion of fragrances into the atmosphere, the devices are cumbersome to handle and expensive to manufacture, and are complex in design in comparison to the simple fragrance releasing element of the present invention.

Recently, mushroom shaped containers have been marketed which release a fragrance from a reservoir into the atmosphere through a film housed in the upper portion of the mushroom shaped container. Such devices are typified by U.S. Pat. No. 4,793,555, issued Dec. 27, 1988. While such devices are effective for their intended purpose, they still suffer from the disadvantage of the presence of a liquid fragrance within the container and the opportunity for spillage or leakage of the liquid from the container, which can be troublesome. Such disadvantages are sought to be overcome with the devices of the present invention in that such devices contain no liquid fragrance which can be spilled or leaked from the hourglass container, but rather the fragrance is entrapped within a porous carrier particulate material which is free flowing.

The concept of producing spheres or beads by means of suspension polymerization techniques is well known in the prior art. An exemplary one of such processes is disclosed in U.S. Pat. No. 2,809,943, issued Oct. 15, 1957. However, it was found that when a material was added which is a solvent for the monomers, but acts as a precipitant for the resulting polymer, a novel form of bead was provided containing a network of microscopic channels. This discovery is set forth in U.S. Pat. No. 4,224,415, filed July 18, 1958, issuing some twenty-two years later on Sept. 23, 1980. In this patent, beads are produced ranging in size from about 350 to about 1200 microns. Typical monomers include divinyl toluene, diallyl maleate, and triallyl phosphate. The precipitant employed is an alkane, acid ester, or alcohol.

This technology was expanded and the precipitant was variously described in the patent literature as a diluent, porogen, active ingredient, solvent, functional material, and volatile agent. For example, in U S. Reissue Pat. No. 27,026, issued Jan. 12, 1971, porous beads of a diameter less than ten microns are disclosed. Among the monomers used to produce the beads are ethyl methacrylate, divinyl benzene, and ethylene glycol dimethacrylate. In U.S. Pat. No. 3,418,262, issued Dec. 24, 1968, there is described a bead characterized as having a rigid sponge structure, and wherein the porogenic agent employed is an acid such as stearic acid. Intermediates in bead form were produced in U.S. Pat. No. 3,509,078, issued Apr. 28, 1970, using polymeric materials such as polyethylene glycols as the precipitant material during the in situ suspension polymerization process. The macroporous character of such bead construction is graphically portrayed and illustrated in FIG. 1 of U.S. Pat. No. 3,627,708, issued Dec. 14, 1971. Beads termed "pearls" are produced, and containing active ingredients therein such as water or various alcohol ethers. The pearls are crosslinked to the extent of about twenty percent. In U.S. Pat. No. 3,637,535, issued Jan. 25, 1972, beads with a sponge structure are said to be capable of being compressed to an imperceptible powder. These beads are capable of being loaded with as much as 200–300% of active ingredients such as white spirit and benzin. A rigid porous bead of a trifunctional methacrylate is taught in U.S. Pat. No. 3,767,600, issued Oct. 23, 1973. Such beads have a size of 10–900 microns, and various other monomers which can be employed include diacetone acrylamide, and ethylhexyl, hydroxyethyl, and hydroxypropyl methacrylates. Paraffin wax in an amount of 5–100% is used to form the microscopic network of channels in U.S. Pat. No. 3,989,649, issued Nov. 2, 1976. The wax may be removed from the bead structure by solvent extraction.

While many of the foregoing U.S patents relate to ion exchange technology, a bead similar to those previously described is employed as a carrier for enzymes in U.S. Pat. No. 4,208,309, issued June 17, 1980. Such beads are of the size of about 0.1 mm. U.S. Pat. No. 4,661,327, issued Apr. 28, 1987 describes a macroreticular bead containing a magnetic core. The use of hard crosslinked porous polymeric beads in cosmetics as carriers is taught in U.S. Pat. No. 4,724,240, issued Feb. 9, 1988, wherein various emollients and moisturizers are entrapped therein. These beads are said to be capable of entrapping materials such as 2-ethylhexyl oxystearate, arachidyl propionate, petroleum jelly, mineral oil, lanolin, and various siloxanes. The size of the beads ranges from 1–3,000 microns. Typical monomers include ethylene glycol dimethacrylate, lauryl methacrylate, trimethylol propane trimethacrylate, and dipentaerythritol dimethacrylate. "In situ" hydrophobic powders and "in situ" beads may be produced in accordance with the teaching of this patent. Beads having a rigid sponge structure are also described in U.S. Pat. No. 4,690,825, issued Sept. 1, 1987, and wherein the beads function as a delivery vehicle for a host of materials including pigments, vitamins, fragrances, drugs, repellants, detergents, and sunscreens. The beads have a size of 10–100 microns and are preferably of a monomer system of styrene-divinyl benzene. Crosslinking is said to range from 10–40 percent. U.S. Pat. No. 4,806,360, issued Feb. 21, 1989, describes a post adsorbent bead which contains a melanin pigment for use as a sunscreen.

The foreign patent literature includes West German Offenlegungsschrift No. P-2608533.6, Published Sept. 30, 1976, and wherein porous polymeric beads produced by "in situ" suspension polymerization are provided, and which are adapted to release perfumes A controlled release of the fragrance is disclosed, providing utility for such beads in the home, automobiles, airplanes, railway cars, hospitals, classrooms, conference centers, and gymnasiums. Canadian Pat. No. 1,168,157, issued May 29, 1984, describes hard, discrete, free flowing, bead constructions in which the beads entrap a series of functional materials which can be incorporated into toilet soap, body powder, and antiperspirant sticks. The Canadian Patent, it is noted, is the equivalent of European Pat. No. 61,701, issued on July 16, 1986, both of which are foreign equivalents of the parent case of the '240 patent. In European International Publication No. 0252463A2, published Jan. 13, 1988, there is disclosed a bead having a hydrophobic polymer lattice, and which entraps numerous non-cosmetic materials such as pesticides, pharmaceuticals, pheromones, and various categories of chemicals. Steroids are entrapped, for example, in the porous beads of PCT International Publication No. WO-88/01164, published on Feb. 25, 1988. The steroids are adrenocortical steroids or various anti-inflammatory type steroids. It should therefore be apparent that what began as a simple ion exchange bead concept has rapidly grown into a technology of widely varied application.

Thus, according to the prior art, crosslinked porous copolymers in particle form can be produced by at least three distinct processes. One process produces beads by "in situ" suspension polymerization. Another process produceS beads by suspension polymerization but the beads are "post adsorbed" with an active ingredient after the volatile porogen is removed. In a third process, powders are produced by "in situ" precipitation polymerization What has been accomplished in accordance with the present invention, however, is a unique concept differing from all of the foregoing methods, and wherein post adsorbent powders and beads are used in a novel fashion.

SUMMARY OF THE INVENTION

This invention relates to a fragrance releasing device in the form of a container having at least two chambers, means forming a channel for providing communication between the two chambers, porous particulate carrier means in one of said chambers, and a fragrance contained and entrapped within the carrier means.

One chamber of the container is constructed of an air impermeable material. The other chamber of the container is constructed of an air permeable material. The shape of each chamber of the container is symmetrical, and the container is preferably formed in the shape of an hourglass. The channel forming means provides a reduced and restricted flow passageway between the two chambers. The passageway is of a diameter substantially less than the diameter of the two chambers and of a size sufficient for allowing passage of the particulate carrier means from one chamber to the other when the container is inverted.

The particulate carrier means can be in the form of micron-sized beads, or the particulate carrier means can be in the form of a powder. In the latter case, the powder constitutes a combined system of particles, the system of powder particles including unit particles of a size less than about one micron in average diameter, agglomerates of fused unit particles of sizes in the range of about twenty to about eighty microns in average diameter, and aggregates of clusters of fused agglomerates of sizes in the range of about two hundred to about twelve hundred microns in average diameter. Both the beads and the powder are formed of a highly cross-linked polymethacrylate copolymer.

During shipment and before the fragrance releasing device of the present invention is employed for consumer use, blocking means are arranged in the passageway for preventing movement of the particulate carrier means from one chamber of the container to the other chamber of the container. The blocking means is inactivated when the device is put into use. The two chambers of the container are also formed of a transparent material in order that the contents of the chambers are rendered visible. Thus, the consumer is able to visually inspect the contents of the hourglass as the porous particulate carrier including the entrapped fragrance trickles from one chamber to the other. As one chamber is filled, the container can be inverted to alternately actuate or deactuate the fragrance releasing function of the device of the present invention.

The fragrance releasing device described herein has utility in many areas. For example, the devices may be employed in the household and placed upon bathroom toilet bowls, adjacent trash cans, in kitchen cabinets, closets, on refrigerators, in windows, and in laundry rooms. Another practical application of the devices is for automobiles and boats. The devices can be arranged on dashboards, in glove compartments, or in rear window areas. Industrially, the devices can be placed in restrooms, offices, hallways, conferences rooms, and in manufacturing facilities.

It is therefore an object of the present invention to eliminate or substantially reduce the initial and undesirable high concentration burst of conventional fragrance, cologne, and perfume, controlled release devices, which occurs immediately following application of such devices including aerosols.

It is also an object of the present invention to provide for the controlled release of fragrances. colognes, and perfumes, at a constant rate as against time in a reservoir-type device.

It is a further object of the present invention to provide for the sustained release of fragrances, colognes and perfumes, in order to insure effective release of the fragrance, cologne, and perfume, for periods of weeks in household and industrial applications.

The porous particulate carrier means is a macroporous, cross-linked, copolymer produced in a reactor equipped with a stirrer, by precipitation polymerization in a solvent containing at least one monounsaturated monomer and at least one polyunsaturated monomer soluble therein, and conducting the polymerization in the reactor at stirring rates of from zero revolutions per minute to about three hundred revolutions per minute.

The solvent is removed from the porous copolymer at the conclusion of the polymerization, in which case, the copolymer is mixed with a functional fragrance material in order to disperse and uniformly distribute the functional material throughout the porous copolymer, and to entrap the functional material therewithin.

One monomer of the copolymer is a monounsaturated monomer such as lauryl methacrylate, and the other monomer of the copolymer is a polyunsaturated monomer such as ethylene glycol dimethacrylate. The copolymer can also be formed using only polyunsaturated monomers. The copolymer is in the form of a powder and the powder is a combined system of particles. The system of powder particles includes unit particles of less than about one micron in average diameter, agglomerates of fused unit particles of sizes in the range of about twenty to eighty microns in average diameter, and aggregates of clusters of fused agglomerates of sizes in the range of about two hundred to about twelve hundred microns in average diameter.

A precipitation polymerization process is used for producing the macroporous cross-linked copolymer. In the process, there is copolymerized at least one monounsaturated monomer and at least one polyunsaturated monomer in the presence of an organic liquid which is a solvent for the monomers but not for the copolymer. The process can also be conducted using only polyunsaturated monomers. The copolymerization of the monomers is initiated by means of a free radical generating catalytic compound, precipitating a copolymer in the solvent in the form of a powder. A dry powder is formed by removing the solvent from the precipitated copolymeric powder.

The solvent is preferably isopropyl alcohol, although ethanol, toluene, heptane, xylene, hexane, ethyl alcohol, and cyclohexane may also be employed. The monounsaturated monomer and the polyunsalurated monomer can be present in mol ratios of, for example, 20:80, 30:70, 40:60, or 50:50. The process includes the step of stirring the monomers, solvent, and the free radical generating catalytic compound, during copolymerization. Preferably, the dry powder is formed by filtering excess solvent from the precipitated powder, and the filtered powder is vacuum dried. The powder may then be "post adsorbed" with various functional fragrance materials.

These and other objects features, and advantages, of the present invention will become apparent when considered in light of the following detailed description, including the accompanying drawings.

IN THE DRAWINGS

Figure 1:
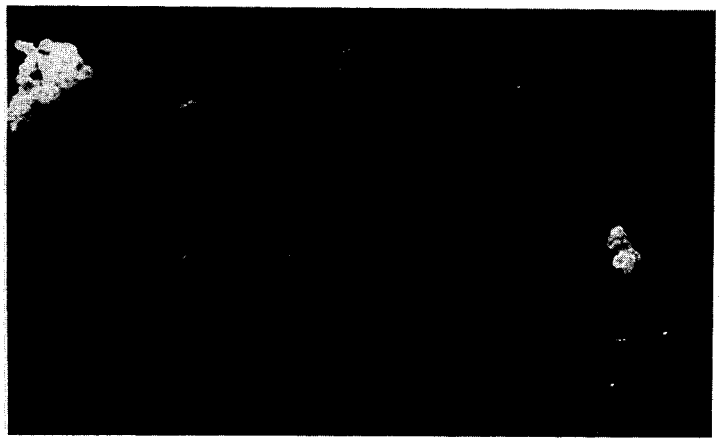
FIG. 1 is a photomicrograph of the various components of the complex structure of the powder produced in Example I, and including unit particles, agglomeratures, and aggregates.
Figure 2:
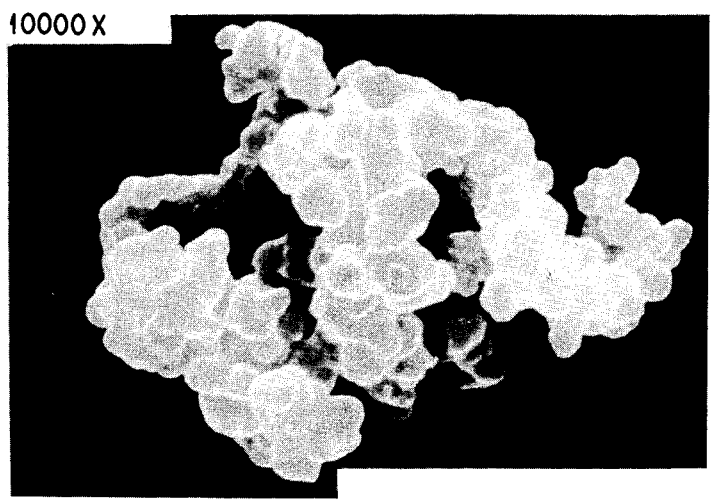
FIGS. 2 and 3 are photomicrographs of the agglomerates and aggregates of FIG. 1, respectively, shown on a larger scale.
Figure 3:
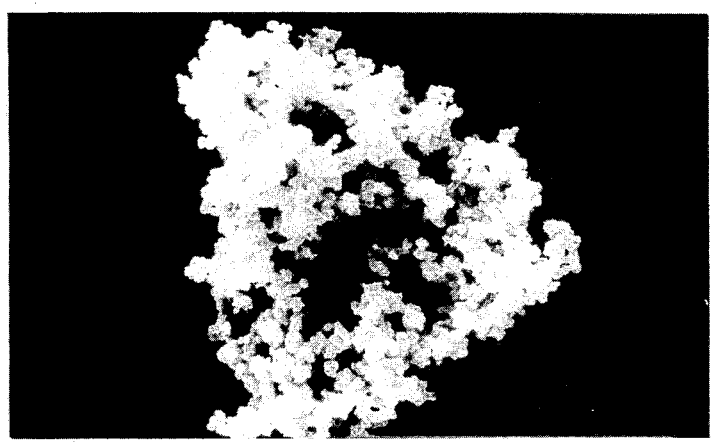

In the above figures in the drawing, the magnification is indicated in each instance. For example, the magnification in FIGS. 6-9 is 1000X, and 2000X in FIG. 10. FIGS. 6-10 also include an insert identifying a length approximating ten microns for comparative purposes.

It should be pointed out, that in viewing the various figures, one will note that as the rate of stirring is increased from zero rpm up to eight hundred rpm, that the size of the unit particles increase. This is in direct opposition to what has been traditionally observed in suspension polymerization systems, wherein increases in stirring rates decrease particle size. Because of the increased size of the unit particles shown in FIG. 10 and the resulting decrease in surface area, the adsorptive capacity of these large particles is less than the adsorptive capacity of the smaller sized particles shown in FIGS. 6-9.

The most effective unit particles can be produced if the rate of stirring is maintained below about three hundred rpm, although particles produced at rates beyond three hundred rpm are useful and adsorptive, but to a lesser extent.

FIG. 11 is a pictorial representation of a fragrance releasing device in accordance with the present invention and depicting the hourglass shaped container including the porous particulate carrier having the fragrance entrapped therein and with the fragrance loaded carrier occupying one of the container chambers and flowing into the other chamber. The device includes a frame assembly for holding the hourglass upright and for decorative purposes.

FIG. 12 is a pictorial representation partly in cross-section illustrating the hourglass container of the present invention including a stopcock arranged in the flow channel for controlling the flow of the porous particulate carrier between the two chambers.

FIG. 13 is a partial view of an alternate embodiment of the present invention and illustrating a portion of the channel between the two chambers of the hourglass.

FIG. 14 is a pictorial representation of another embodiment of the present invention and illustrating the hourglass container with a removable plug in the flow channel.

DETAILED DESCRIPTION OF THE INVENTION

The material of the present invention, can be broadly and generally described as a crosslinked copolymer capable of entrapping solids, liquids, and gases. The copolymer is in particulate form and constitutes free flowing discrete solid particles even when loaded with an active material. When loaded, it may contain a predetermined quantity of the active material. One copolymer of the invention has the structural formula:

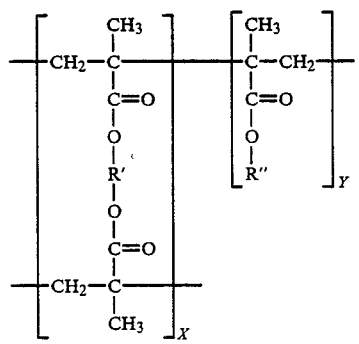

where the ratio of x to y is 80:20, R' is —$CH_2CH_2$—, and R" is —$(CH_2)_{11}CH_3$.

The copolymer is a highly crosslinked copolymer, as evidenced by the foregoing structural formula, and is more particularly a highly crosslinked polymethacrylate copolymer. This material is manufactured by the Dow Corning Corporation, Midland, MI, U.S.A., and sold under the trademark POLYTRAP$^R$. It is a low density, highly porous free-flowing white particulate, and the particles are capable of adsorbing high levels of lipophilic liquids and some hydrophilic liquids, while at the same time maintaining a free-flowing particulate character.

In the powder form, the structure of the particulate is complex, and consists of unit particles less than one micron in average diameter. The unit particles are fused into agglomerates of twenty to eighty microns in average diameter. These agglomerates are loosely clustered into macro-particles termed aggregates of about 200 to about 1200 microns in average diameter.

Adsorption of fragrance actives to form post adsorbent powder, can be accomplished using a stainless steel mixing bowl and a spoon, wherein the active ingredient is added to the empty dry powder, and the spoon is used to gently fold the active into the powder. Low viscosity fluids may be adsorbed by addition of the fluids to a sealable vessel containing the powder and tumbling the materials until a consistency is achieved. More elaborate blending equipment such as ribbon or twin cone blenders can also be employed.

The following example illustrates the method for making a post adsorbent powder, of the type illustrated in FIGS. 1-3 and 6-10.

EXAMPLE I

A hydrophobic porous copolymer was produced by the precipitation polymerization technique by mixing in a five hundred milliliter polymerization reactor equipped with a paddle type stirrer, 13.63 grams of ethylene glycol dimethacrylate monomer, or eighty mole percent, and 4.37 grams of lauryl methacrylate monomer, or twenty mole percent. Isopropyl alcohol was added to the reactor as the solvent in the amount of 282 grams. The monomers were soluble in the solvent, but not the precipitated copolymer. The process can be conducted with only polyunsaturated monomers if desired. The mixture including monomers, solvent, and 0.36 grams of catalytic initiator benzoyl peroxide, was purged with nitrogen. The system was heated by a water bath to about sixty degrees Centigrade until copolymerization was initiated, at which time, the temperature was increased to about 70-75 degrees Centigrade for six hours, in order to complete the copolymerization. During this time, the copolymer precipitated from the solution. The copolymerization produced unit particles of a diameter less than about one micron. Some of the unit particles adhered together providing agglomerates of the order of magnitude of about twenty to eighty microns in diameter. Some of the agglomerates adhered further and were fused and welded one to another, forming aggregates of loosely held assemblies of agglomerates of the order of magnitude of about two to eight hundred microns in diameter. The mixture was filtered to remove excess solvent, and a wet powder cake was tray dried in a vacuum oven. A dry hydrophobic copolymeric powder consisting of unit particles, agglomerates, and aggregates was isolated.

The adsorptive capacity of the hydrophobic particulates reduced in Example I, as a function of the stirring rate, was determined. The stirring rate during the reaction in Example I significantly influenced the adsorption properties of the particulate materials. The adsorptivity of the particulate materials decreases with an increase in stirring rate, and the density of the particulates increases. These results are set forth in Tables I–III.

TABLE I

| Agitation Rate (RPM) | Bulk Density Size (g/cc) | Average Aggregate Size (μ) | Average Agglomerate Size (μ) | Average Unit Particle Size (μ) | Adsorption Capacity* |
| --- | --- | --- | --- | --- | --- |
| 0 | 0.067 | 182.5 | 33.9 | 1.0 | 83.0 |
| 75 | 0.077 | 140.6 | 36.6 | 0.5 | 84.8 |
| 150 | 0.071 | 149.8 | 39.8 | 0.8 | 83.0 |
| 300 | 0.293 | 47.0 | 34.0 | 1.5–2.0 | 58.3 |
| 800 | 0.440 | — | 10.0 | 3.0–5.0 | 37.7 |

*= Percent Silicone Oil

TABLE II

| Stirring Speed RPM | Adsorption Capacity % | | | |
| --- | --- | --- | --- | --- |
| | Water | Mineral Oil | Glycerine | Organic Ester* |
| 0 | 0 | 80 | 75 | 80 |
| 75 | 0 | 83.9 | 75 | 81.5 |
| 150 | 0 | 80 | 75 | 80 |
| 300 | 0 | 54.5 | 58.3 | 54.5 |

*= 2-ethylhexyl-oxystearate

TABLE III

| RPM | Adsorption Capacity % | | | Density (g/cm$^3$) | |
| --- | --- | --- | --- | --- | --- |
| | Mineral Oil | 2-ethylhexyl oxystearate | Silicone Oil | Bulk | Tapped |
| 0 | 82.5 | 82.5 | 86.5 | 0.0368 | 0.0580 |
| 75 | 82.3 | 82.2 | 86.5 | 0.0462 | 0.0667 |
| 150 | 82.3 | 82.3 | 86.3 | 0.0527 | 0.0737 |
| 200 | 81.5 | 81.5 | 85.7 | 0.0554 | 0.0752 |
| 250 | 79.2 | 80.0 | 84.8 | 0.0636 | 0.0859 |
| 300 | 68.8 | 68.8 | 75.0 | 0.1300 | 0.1768 |
| 450 | 58.3 | 58.3 | 61.5 | 0.1736 | 0.2392 |
| 600 | 54.5 | 54.5 | 60 | 0.1933 | 0.2792 |
| 700 | 42.2 | 42.5 | 45.7 | 0.2778 | 0.4142 |
| 800 | 33.3 | 28.6 | 33.3 | 0.3862 | 0.5322 |
| 1000 | 32.8 | 28.5 | 32.9 | 0.3808 | 0.5261 |

In the foregoing tables, it can be seen that adsorption and density, as a function of stirring rate, was determined for several fluids including a silicone oil, water, mineral oil, glycerine, and an organic ester. From zero rpm up to about 250 rpm, the adsorptivity of the porous copolymeric powder particulates of Example I remained essentially consistent. However, at about three hundred rpm, there was a substantial decrease in adsorptivity, which decrease became more apparent as the stirring rate was increased up to about one thousand rpm. A similar pattern is evidenced by the data which are reflective of the density.

This phenomenon is more apparent in the photomicrographic figures of the drawing. Thus, it can be seen from FIG. 6, that the particle size of the unit particles increases as the stirring rate is increased, as evidenced by FIG. 10. A progression in this phenomenon can be obserVed in FIGS. 7–9.

While the procedure of Example I is a precipitation polymerization process and not a suspension polymerization system, the prior art dealing with suspension polymerization processes, teaches that an increase in stirring rate causes a decrease in particle size. This is documented, for example, in U.S. Pat. No. 4,224,415, issued Sept. 23, 1980, and in the PCT International Publication. The PCT International Publication employs stirring rates upwards of nine hundred to twelve hundred rpm. In Example I of the present invention, however, increases in stirring rates not only did not decrease the particle size, but in fact had exactly the opposite effect, causing the unit particle size to increase. As the rate of stirring increased from zero rpm up to one thousand, the density of the particles increased and the adsorptive capacity decreased.

In accordance with the above, it is possible to tailor porous adsorbent powders of a particular particle size and adsorptivity by means of stirring rate. Thus, with large unit particles in FIG. 10, the adsorptive capacity is less than the adsorptive capacity of smaller sized unit particles in FIGS. 6–9. While the most effective particles are produced when the rate of stirring is maintained below about three hundred rpm, particles produced at rates beyond three hundred rpm are useful.

Figure 4:
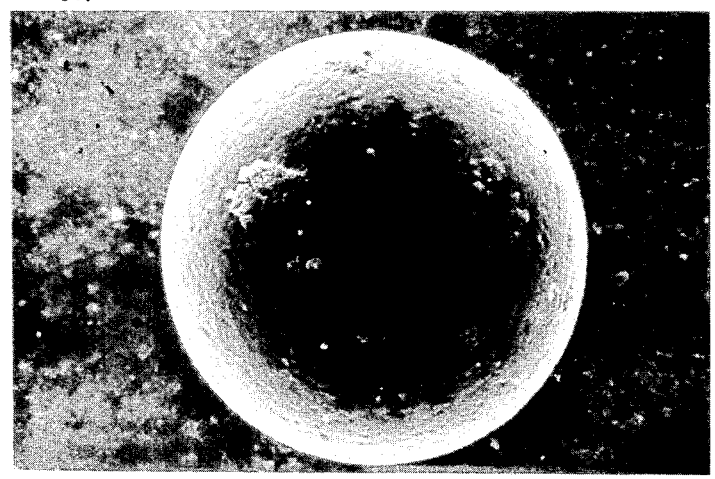
FIG. 4 is a photomicrograph of a polymer bead produced by suspension polymerization.
Figure 5:
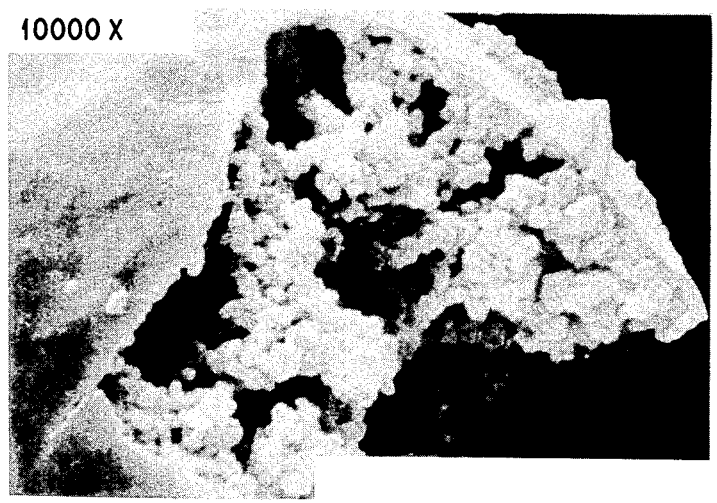
FIG. 5 is a photomicrograph of the bead of FIG. 4 with a portion of the shell removed to reveal the interior structure of the bead.
Figure 6:
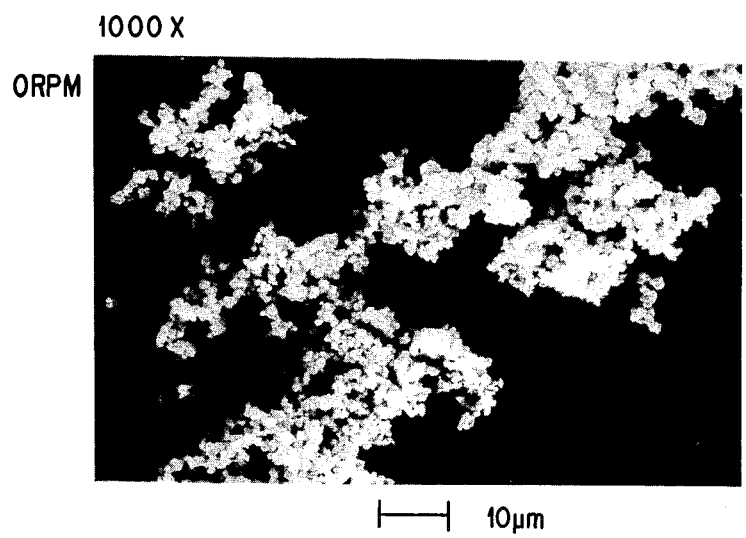
FIG. 6 is a photomicrograph of a copolymeric powder material. The powder is shown in magnification as it appears when the agitation rate employed in the process for producing the powder is zero rpm.
Figure 7:
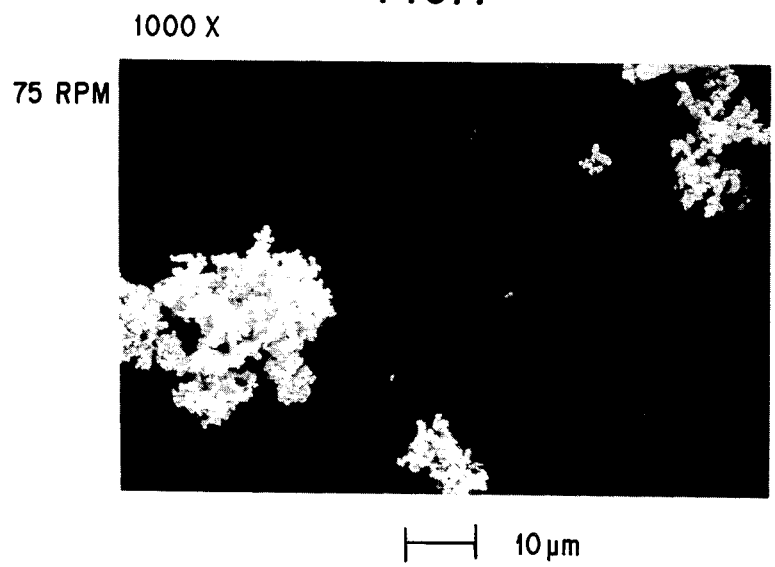
FIGS. 7-10 are additional photomicrographs of copolymeric powder materials. The powder is shown in magnification as it appears when the agitation rate employed in the process for producing the powder varies from seventy-five rpm up to eight hundred rpm.
Figure 8:
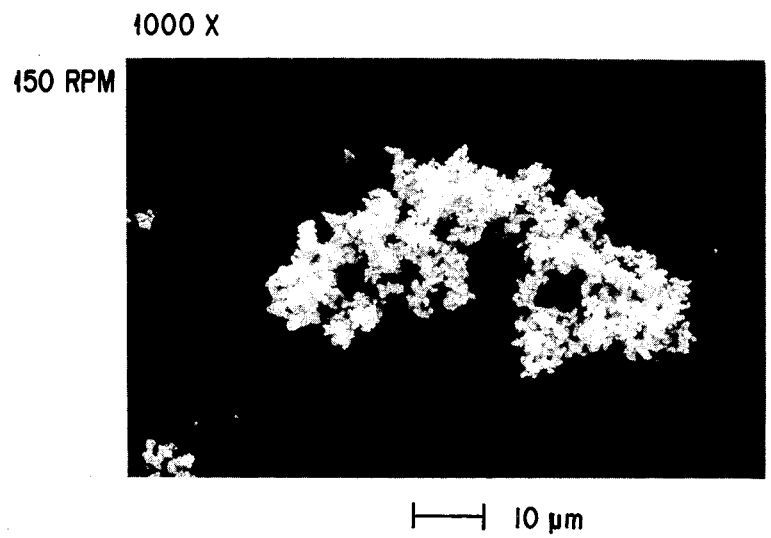
Figure 9:
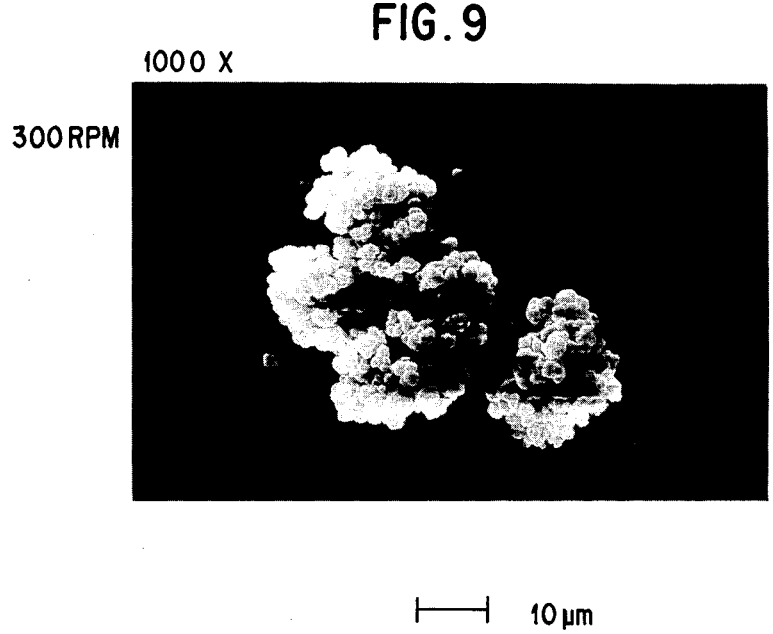
Figure 10:
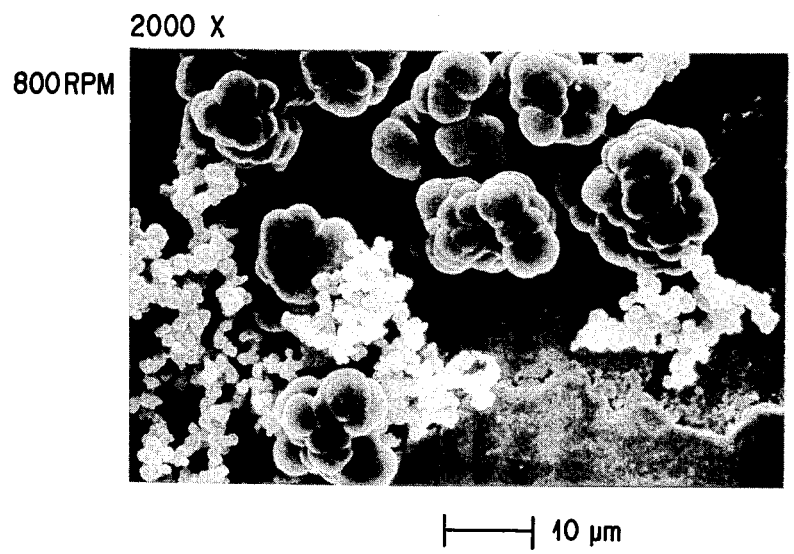

It is important to understand that the method of Example I for the production of porous copolymer particulate powder materials is characterized as a precipitation polymerization technique. In accordance with the technique, monomers are dissolved in a compatible volatile solvent in which both monomers are soluble. Polymer in the form of a powder is precipitated and the polymer is insoluble in the solvent. No surfactant or dispersing aid is required. The materials produced are powders and not spheres or beads. The powder particulates include unit particles, agglomerates, and aggregates. The volatile solvent is subsequently removed resulting in a dry powder, which can be post adsorbed with a variety of functional fragrance ingredients. The suspension polymerization process on the other hand, provides that polymerization be carried out in water, and in some cases chloroform or chlorinated solvents. The monomers, the active, and the catalyst, form beads or droplets in water, and polymerization occurs Within each bead. A surfactant or stabilizer, such as polyvinyl pyrrolidone, is required in order to prevent the individually formed beads and droplets from coalescing. The resulting beads, with the active material entrapped therein, include a substantially spherical outer crust or shell, the interior of which contains a macroporous structure of fused unit particles, agglomerates, and aggregates. The bead is about ten microns in average diameter to about one hundred-fifty microns, depending upon the rate of agitation employed during the process. Such beads are shown in FIGS. 4 and 5, and the process is set forth in Example III.

Some unique features of the powders of Example I and FIGS. 1–3 and 6–10 are their ability to adsorb from sixty to eighty percent of a liquid and yet remain free flowing. The materials provide a regulated release of volatile ingredients entrapped therein, and have the capability of functioning as carriers. Loaded powders disappear when rubbed upon a surface. This phenomenon is believed due to the fact that large aggregates of the material scatter light rendering the appearance of a white articulate, however, upon rubbing, these large aggregates decrease in size approaching the range of visible light and hence seem to disappear. The materials do not swell in common solvents and are capable of physically adsorbing active fragrance ingredients by the filling of interstitial voids by capillary action. The active ingredients are subsequently released by capillary action or wicking from the voids within the particulates.

The following example illustrates a precipitation polymerization process in which an organic ester is entrapped "in situ" in the polymer powder.

EXAMPLE II 7 grams of 2-ethylhexyl oxystearate was mixed with 1.5 grams of ethylene glycol dimethacrylate and 1.5 grams of lauryl methacrylate in a glass test tube. The solution was deaerated for five (5) minutes and 0.1 ml of t-butyl peroctoate was added and mixed while heating to 80 degrees Centigrade in an oil bath. After 20 minutes, the contents solidified; and the mixture was maintained at about 80 degrees Centigrade for an additional hour to assure full polymerization. A semi-soft, heterogeneous white opaque polymer mass resulted containing the entrapped ester.

The powder of Example II differs from the powder of Example I in that the solvent in Example I is removed resulting in a dry empty powder which is post adsorbed with other functional materials. The powder of Example II is otherwise similar to the material shown in FIGS. 1–3.

Example III illustrates a process for the production of beads as shown in FIGS. 4 and 5. The process is suspension polymerization and an organic ester is entrapped "in situ".

EXAMPLE III 1.20 grams of polyvinyl pyrrolidone was dissolved in 1500 ml of water in a 2000 ml three necked resin flask equipped with a stirrer, thermometer and nitrogen purge. A solution of 335 grams of 2-ethylhexyl oxystearate, 132 grams ethylene glycol dimethacrylate, 33 grams 2-ethylhexyl methacrylate, and 5 ml t-butyl peroctoate, was bubbled with nitrogen for 5 minutes. The resultant mix was slowly added to the stirred aqueous solution of polyvinyl pyrrolidone at 22 degrees Centigrade under nitrogen. The temperature was raised to 80 degrees Centigrade with constant agitation and held until polymerization started in approximately 15 minutes, and maintained at 80 degrees Centigrade for an additional 2 hours to complete the reaction Semi-soft, white opaque beads were collected by filtering off the supernatant liquid and dried to remove any excess water. The beads weighed 450 g for a yield of 90%, and were 0.25 to 0.5 mm in diameter. Other protective colloids such as starch, polyvinyl alcohol, carboxymethyl cellulose, methyl cellulose, or inorganic systems such as divalent alkali metal hydroxides, for example MgOH, may be used in place of the polyvinyl pyrrolidone suspending medium.

In Example III macroporous polymers submicron in size are produced with two or more monomers, at least one monomer of which contains more than a single double bond. The polymerization is conducted in the presence of an active ingredient which does not dissolve or swell the resulting polymer. The monomers and the active ingredient are mutually soluble, but are insoluble in the aqueous suspending medium in which droplets are formed. Polymerization occurs within suspended droplets, and beads or spheres are produced. The active ingredient which is polymerized "in situ" is entrapped and contained within the beads, but the active ingredient is capable of being released. It is also possible to use a volatile liquid during polymerization, and to subsequently thermally drive off the volatile liquid, leaving behind a porous polymer bead product into which a variety of active fragrance materials can be subsequently adsorbed.

Examples of polyunsaturated monomers suitable for use in accordance with the present invention are ethylene glycol dimethacrylate, triethylene glycol dimethacrylate, tetraethylene glycol dimethacrylate, trimethylol propane ethoxylated triacrylate, ditrimethylol propane dimethacrylate; propylene, dipropylene and higher propylene glycols, 1,3 butylene glycol dimethacrylate, 1,4 butanediol dimethacrylate, 1,6 hexanediol dimethacrylate, neopentyl glycol dimethacrylate, pentaerythritol dimethacrylate, dipentaerythritol dimethacrylate, bisphenol A dimethacrylate, divinyl and trivinyl benzene, divinyl and trivinyl toluene triallyl maleate, triallyl phosphate, diallyl maleate, diallyl itaconate, and allyl methacrylate. The monounsaturated monomers include allyl methacrylates and acrylates having straight or branched chain alkyl groups with 1 to 30 carbon atoms, preferably 5 to 18 carbon atoms. Preferred monomers include lauryl methacrylate, 2-ethylhexyl methacrylate, isodecylmethacrylate, stearyl methacrylate, hydroxy ethyl methacrylate, hydroxy propyl methacrylate, diacetone acrylamide, phenoxy ethyl methacrylate, tetrahydrofurfuryl methacrylate and methoxy ethyl methacrylate.

As noted previously, the copolymer can be formed by copolymerizing one monounsaturated monomer with one polyunsaturated monomer, or with only polyunsaturated monomers.

EXAMPLE IV

Example I was repeated for each of a series of monomer systems shown in Tables IV–XVII. In each instance, submicron sized copolymeric powders were produced employing a stirring speed of about seventy-five RPM. The catalyst was dibenzoyl peroxide. Absorption capacities of the various copolymeric powder for fluids were determined and are shown in the Tables, along with the mole ratios of monomers and the solvent. The abbreviations used in Tables IV–XVII are identified as follows:

| | |
|---|---|
| DAA | Diacetone acrylamide |
| EGDM | Ethylene glycol dimethacrylate |
| TEGDM | Tetraethylene glycol dimethacrylate |
| ST | Styrene |
| DVB | Divinylbenzene |
| VP | Vinyl pyrrolidone |
| IBOMA | Isobornyl methacrylate |
| PEMA | Phenoxyethyl methacrylate |
| IDMA | Isodecyl methacrylate |
| STMA | Stearyl methacrylate |
| HPMA | Hydroxypropyl methacrylate |
| CYMA | Cyclohexyl methacrylate |
| DMAEMA | Dimethylaminoethyl methacrylate |
| TBAEMA | t-butyl aminoethyl methacrylate |
| AMPS | 2-acrylamido propane sulfonic acid |
| BMA | Butyl methacrylate |
| EHMA | 2-ethylhexyl methacrylate |
| MMA | Methyl methacrylate |
| HEMA | 2-hydroxyethyl methacrylate |
| EHO | 2-ethylhexyl oxystearate |

| | |
|---|---|
| GG | Glucose glutamate |
| IPA | Isopropyl alcohol |
| PEG | Polyethylene glycol 200 |

TABLE IV

| Monomers | Mole Ratio | Solvent | Adsorption Capacity % | | | |
|---|---|---|---|---|---|---|
| | | | EHO | Glycerine | GG | Water |
| DAA/EGDM | 20/80 | Xylene | 75 | 82 | 83 | 78 |
| DAA/EGDM | 30/70 | Xylene | 77 | 80 | 83 | 78 |
| DAA/EGDM | 40/60 | Xylene | 75 | 75 | 83 | 77 |
| DAA/EGDM | 50/50 | Xylene | 50 | 57 | 67 | 0 |
| DAA/EGDM | 60/40 | Xylene | 40 | 40 | 50 | 0 |
| DAA/TEGDM | 20/80 | Xylene | 40 | 50 | 62 | 58 |
| DAA/TEGDM | 30/70 | Xylene | 29 | 40 | 50 | 55 |
| DAA/TEGDM | 40/60 | Xylene | 25 | 28 | 40 | 43 |
| DAA/TEGDM | 50/50 | Xylene | 25 | 30 | 40 | 43 |
| DAA/TEGDM | 60/40 | Xylene | 22 | 29 | 40 | 40 |

TABLE V

| Monomers | Mole Ratio | Solvent | Adsorption Capacity % | | | |
|---|---|---|---|---|---|---|
| | | | EHO | Glycerine | PEG | Water |
| ST/TEGDM | 20/80 | IPA | 58 | 69 | 69 | 67 |
| ST/TEGDM | 30/70 | IPA | 58 | 64 | 67 | 69 |
| ST/TEGDM | 40/60 | IPA | 62 | 71 | 71 | 61 |
| ST/TEGDM | 50/50 | IPA | 67 | 62 | 54 | 58 |
| ST/TEGDM | 60/40 | IPA | 50 | 58 | 58 | 54 |
| ST/TEGDM | 70/30 | IPA | 50 | 58 | 50 | 54 |
| ST/TEGDM | 80/20 | IPA | 44 | 54 | 50 | 50 |
| ST/DVB | 20/80 | IPA | 80 | 75 | 75 | 0 |
| ST/DVB | 30/70 | IPA | 75 | 67 | 75 | 0 |
| ST/DVB | 40/60 | IPA | 69 | 67 | 67 | 0 |
| ST/DVB | 50/50 | IPA | 64 | 72 | 67 | 0 |
| ST/DVB | 60/40 | IPA | 67 | 71 | 71 | 0 |
| ST/DVB | 70/30 | IPA | 71 | 75 | 76 | 0 |
| ST/DVB | 80/20 | IPA | 50 | 50 | 50 | 0 |

TABLE VI

| Monomers | Mole Ratio | Solvent | Adsorption Capacity % | | | |
|---|---|---|---|---|---|---|
| | | | EHO | Glycerine | GG | Water |
| VP/EGDM | 20/80 | Xylene | 77 | 80 | 74 | 73.6 |
| VP/EGDM | 30/70 | Xylene | 76 | 79 | 78.3 | 70 |
| VP/EGDM | 40/60 | Xylene | 70 | 67 | 75.6 | 75 |
| VP/EGDM | 50/50 | Xylene | 72 | 76 | 80 | 76 |
| VP/EGDM | 60/40 | Xylene | 74 | 80 | 76 | 77 |
| VP/EGDM | 70/30 | IPA | 71 | 78 | 74 | 75 |
| VP/EGDM | 80/20 | IPA | 67 | 75 | 73 | 74 |
| VP/TEGDM | 20/80 | Xylene | 58 | 68.8 | 61.5 | 67.7 |
| VP/TEGDM | 30/70 | Xylene | 70 | 67 | 54.5 | 68.8 |
| VP/TEGDM | 40/60 | Xylene | 54.5 | 61.5 | 52.4 | 64.3 |
| VP/TEGDM | 50/50 | Xylene | 44.4 | 47.4 | 52.4 | 52.4 |
| VP/TEGDM | 60/40 | Xylene | 50 | 44.4 | 50 | 54.4 |
| VP/TEGDM | 70/30 | Xylene | 50 | 47.4 | 44.4 | 50 |
| VP/TEGDM | 80/20 | Xylene | 54.5 | 52.4 | 60 | 58 |

TABLE VII

| Monomers | Mole Ratio | Solvent | Adsorption Capacity % | | | |
|---|---|---|---|---|---|---|
| | | | EHO | Glycerine | GG | Water |
| IBOMA/EGDM | 20/80 | IPA | 62.9 | 9.1 | 71.4 | 0 |
| IBOMA/EGDM | 30/70 | IPA | 64.3 | 16.6 | 67.7 | 0 |
| IBOMA/EGDM | 40/60 | IPA | 68.7 | 28.6 | 61.5 | 0 |
| IBOMA/EGDM | 50/50 | IPA | 67.7 | 16.7 | 58.3 | 0 |
| IBOMA/EGDM | 60/40 | IPA | 50 | 23.1 | 50 | 0 |
| IBOMA/EGDM | 70/30 | IPA | 50 | 9.1 | 47.3 | 0 |
| IBOMA/EGDM | 80/20 | IPA | 52.3 | 16.6 | 44.4 | 0 |
| IBOMA/TEGDM | 20/80 | IPA | 66.6 | 62.9 | 61.5 | 0 |
| IBOMA/TEGDM | 30/70 | IPA | 61.5 | 61.5 | 70.6 | 0 |
| IBOMA/TEGDM | 40/60 | IPA | 64.3 | 64.3 | 71.4 | 0 |
| IBOMA/TEGDM | 50/50 | IPA | 61.5 | 66.6 | 67.7 | 0 |
| IBOMA/TEGDM | 60/40 | IPA | 58.3 | 54.5 | 54.5 | 0 |
| IBOMA/TEGDM | 70/30 | IPA | 47.3 | 50 | 41.1 | 0 |
| IBOMA/TEGDM | 80/20 | IPA | 37.5 | 41.1 | 33.3 | 0 |

TABLE VIII

| Monomers | Mole Ratio | Solvent | Adsorption Capacity % | | | |
|---|---|---|---|---|---|---|
| | | | EHO | Glycerine | GG | Water |
| PEMA/EGDM | 20/80 | IPA | 64.3 | 68.7 | 66.6 | 61.5 |
| PEMA/EGDM | 30/70 | IPA | 54.5 | 50 | 54.5 | 44.4 |
| PEMA/EGDM | 40/60 | IPA | 52.3 | 47.3 | 72.2 | 9 |
| PEMA/EGDM | 50/50 | IPA | 54.5 | 33.3 | 62.9 | 0 |
| PEMA/EGDM | 60/40 | IPA | 67.7 | 28.5 | 70.5 | 0 |
| PEMA/EGDM | 70/30 | IPA | 69.7 | 44.4 | 60.7 | 0 |
| PEMA/EGDM | 80/20 | IPA | 66.6 | 68.7 | 66.6 | 0 |
| PEMA/TEGDM | 20/80 | IPA | 58.3 | 56.5 | 66.6 | 58.3 |
| PEMA/TEGDM | 30/70 | IPA | 64.2 | 70.5 | 67.7 | 62.9 |
| PEMA/TEGDM | 40/60 | IPA | 66.6 | 67.7 | 71.4 | 69.7 |
| PEMA/TEGDM | 50/50 | IPA | 66.6 | 70.5 | 73.6 | 72.2 |
| PEMA/TEGDM | 60/40 | IPA | 58.3 | 62.9 | 52.3 | 61.5 |
| PEMA/TEGDM | 70/30 | IPA | 50 | 58.3 | 52.3 | 54.5 |
| PEMA/TEGDM | 80/20 | IPA | 67.7 | 73.6 | 76.1 | 47.3 |

TABLE IX

| Monomers | Mole Ratio | Solvent | Adsorption Capacity % | | | |
|---|---|---|---|---|---|---|
| | | | EHO | Glycerine | PEG | Water |
| IDMA/EGDM | 20/80 | IPA | 55 | 64 | 70 | 0 |
| IDMA/EGDM | 30/70 | IPA | 38 | 50 | 44 | 0 |
| IDMA/EGDM | 40/60 | IPA | 50 | 67 | 69 | 0 |
| IDMA/EGDM | 50/50 | IPA | 58 | 64 | 67 | 0 |
| IDMA/EGDM | 60/40 | IPA | 58 | 69 | 69 | 0 |
| IDMA/TEGDM | 20/80 | IPA | 62 | 70 | 70 | 0 |
| IDMA/TEGDM | 30/70 | IPA | 50 | 62 | 62 | 0 |
| IDMA/TEGDM | 40/60 | IPA | 62 | 67 | 67 | 0 |
| IDMA/TEGDM | 50/50 | IPA | 38 | 44 | 50 | 0 |
| IDMA/TEGDM | 60/40 | IPA | 38 | 55 | 50 | 0 |

TABLE X

| Monomers | Mole Ratio | Solvent | Adsorption Capacity % | | | |
|---|---|---|---|---|---|---|
| | | | EHO | Glycerine | PEG | Water |
| STMA/EGDM | 10/90 | IPA | 66 | 64.3 | 66.7 | 0 |
| STMA/EGDM | 20/80 | IPA | 69 | 63 | 65.5 | 0 |
| STMA/EGDM | 30/70 | IPA | 73–75 | 58.3 | 61.5 | 0 |
| STMA/EGDM | 40/60 | IPA | 69–71 | 54.4 | 58.3 | 0 |
| STMA/EGDM | 50/50 | IPA | 60–63 | 52.4 | 52.4 | 0 |
| STMA/TEGDM | 20/80 | IPA | 50 | 47.4 | 52.4 | 0 |
| STMA/TEGDM | 30/70 | IPA | 50 | 64.3 | 50 | 0 |
| STMA/TEGDM | 40/60 | IPA | 52.4 | 61.5 | 58.3 | 0 |
| STMA/TEGDM | 50/50 | IPA | 47.4 | 52.4 | 56.5 | 0 |

TABLE XI

| Monomers | Mole Ratio | Solvent | Adsorption Capacity % | | | |
|---|---|---|---|---|---|---|
| | | | EHO | Glycerine | PEG | Water |
| HPMA/EGDM | 20/80 | Xylene | 64.3 | 61.5 | 61.5 | 9 |
| HPMA/EGDM | 30/70 | Xylene | 54.5 | 16.7 | 58.3 | 0 |
| HPMA/EGDM | 40/60 | Xylene | 54.5 | 9 | 58.3 | 0 |
| HPMA/EGDM | 50/50 | Xylene | 37.5 | 58.3 | 50 | 0 |
| HPMA/EGDM | 60/40 | Xylene | 44.4 | 61.5 | 58.3 | 0 |
| HPMA/EGDM | 70/30 | Xylene | 50 | 44.4 | 37.5 | 0 |
| HPMA/EGDM | 80/20 | Xylene | 61.5 | 16.7 | 58.3 | 0 |
| HPMA/TEGDM | 20/80 | Xylene | 60 | 58.3 | 54.5 | 61.5 |
| HPMA/TEGDM | 30/70 | Xylene | 56.5 | 54.5 | 50 | 60 |
| HPMA/TEGDM | 40/60 | Xylene | 50 | 58.3 | 52.4 | 54.5 |
| HPMA/TEGDM | 50/50 | Xylene | 52.4 | 61.5 | 54.5 | 56.5 |
| HPMA/TEGDM | 60/40 | Xylene | 33.3 | 47.4 | 44.4 | 54.5 |
| HPMA/TEGDM | 70/30 | Xylene | 54.5 | 44.4 | 54.5 | 50 |
| HPMA/TEGDM | 80/20 | Xylene | 50 | 47.4 | 41.2 | 37.5 |

TABLE XII

| Monomers | Mole Ratio | Solvent | Adsorption Capacity % | | | |
|---|---|---|---|---|---|---|
| | | | EHO | Glycerine | PEG | Water |
| CYMA/EGDM | 80/20 | IPA | 61.5 | 71.4 | 66.6 | 0 |
| CYMA/EGDM | 70/30 | IPA | 60 | 66 | 64.2 | 0 |
| CYMA/EGDM | 60/40 | IPA | 61.5 | 66 | 66.6 | 0 |
| CYMA/EGDM | 50/50 | IPA | 64.2 | 66 | 68.7 | 0 |
| CYMA/EGDM | 40/60 | IPA | 64.2 | 66 | 68.7 | 0 |
| CYMA/EGDM | 30/70 | IPA | 61.5 | 66 | 66.6 | 0 |
| CYMA/EGDM | 20/80 | IPA | 66.6 | 71.4 | 75 | 61.5 |
| CYMA/TEGDM | 80/20 | IPA | 68.7 | 0 | 68.7 | 0 |
| CYMA/TEGDM | 70/30 | IPA | 71.4 | 0 | 69.7 | 0 |
| CYMA/TEGDM | 60/40 | IPA | 66.6 | 0 | 62.9 | 0 |
| CYMA/TEGDM | 50/50 | IPA | | 0 | | 0 |
| CYMA/TEGDM | 40/60 | IPA | 60 | 0 | 72.9 | 0 |
| CYMA/TEGDM | 30/70 | IPA | 64.2 | 0 | 72.2 | 0 |
| CYMA/TEGDM | 20/80 | IPA | 61.5 | 0 | 66.6 | 0 |

TABLE XIII

| Monomers | Mole Ratio | Solvent | Adsorption Capacity % | | | |
|---|---|---|---|---|---|---|
| | | | Water | Mineral Oil | Glycerine | EHO |
| DMAEMA/EGDM | 20/80 | Hexane | 0 | 58.3 | 66.7 | 58.3 |
| DMAEMA/EGDM | 40/60 | Hexane | 66.7 | 61.5 | 70.6 | 66.7 |
| DMAEMA/EGDM | 60/40 | Hexane | 77.3 | 61.5 | 72.2 | 76.2 |
| DMAEMA/EGDM | 80/20 | Hexane | 66.7 | 58.3 | 68.8 | 58.3 |
| TBAEMA/EGDM | 20/80 | Hexane | 0 | 70.6 | 75 | 70.6 |
| TBAEMA/EGDM | 40/60 | Hexane | 0 | 66.7 | 72.2 | 66.7 |
| TBAEMA/EGDM | 60/40 | Hexane | 0 | 61.5 | 68.75 | 61.5 |
| TBAEMA/EGDM | 80/20 | Hexane | 0 | 44.4 | 54.6 | 50 |
| TBAEMA/EGDM | 80/20 | Hexane | 54.6 | 54.6 | 58.3 | 50 |

TABLE XIV

| Monomers | Mole Ratio | Solvent | Adsorption Capacity % | | | |
|---|---|---|---|---|---|---|
| | | | Water | Mineral Oil | Glycerine | EHO |
| AMPS/EGDM | 20/80 | Xylene | 84.3 | 83.3 | 85.3 | 83.3 |
| BMA/EGDM | 20/80 | Hexane | 0 | 70.6 | 75 | 68.8 |
| BMA/EGDM | 40/60 | Hexane | 0 | 70.6 | 77.3 | 70.6 |
| BMA/EGDM | 40/60 | Ethyl-Alcohol | 0 | 66.7 | 73.7 | 68.8 |
| BMA/EGDM | 60/40 | Hexane | 0 | 72.2 | 0 | 73.7 |
| BMA/EGDM | 80/20 | Hexane | 0 | 54.5 | 66.7 | 58.3 |

TABLE XV

| Monomers | Mole Ratio | Solvent | Adsorption Capacity % | | | |
|---|---|---|---|---|---|---|
| | | | Water | Mineral Oil | Glycerine | EHO |
| 2 EHMA/EGDM | 20/80 | IPA | 0 | 68.8 | 66.7 | 64.3 |
| 2 EHMA/EGDM | 30/70 | IPA | 0 | 68.8 | 66.7 | 64.3 |
| 2 EHMA/EGDM | 40/60 | IPA | 0 | 66.7 | 66.7 | 70.6 |
| 2 EHMA/EGDM | 50/50 | IPA | 0 | 64.3 | 68.3 | 61.5 |
| 2 EHMA/EGDM | 60/40 | IPA | 0 | 61.5 | 64.3 | 50 |
| 2 EHMA/EGDM | 70/30 | IPA | 0 | 58.3 | 64.3 | 50 |
| 2 EHMA/EGDM | 80/20 | IPA | 0 | 58.3 | 64.3 | 50 |

TABLE XVI

| Monomers | Mole Ratio | Solvent | Adsorption Capacity % | | | |
|---|---|---|---|---|---|---|
| | | | Water | Mineral Oil | Glycerine | EHO |
| MMA/EGDM | 20/80 | IPA | 61.5 | 58.3 | 64.3 | 58.3 |
| MMA/EGDM | 30/70 | IPA | 64.3 | 61.5 | 66.7 | 61.5 |
| MMA/EGDM | 40/60 | IPA | 61.5 | 64.3 | 64.3 | 61.5 |
| MMA/EGDM | 50/50 | IPA | 58.3 | 54.5 | 61.5 | 58.3 |
| MMA/EGDM | 60/40 | IPA | 54.5 | 50 | 61.5 | 54.5 |
| MMA/EGDM | 70/30 | IPA | 66.7 | 61.5 | 72.2 | 64.3 |
| MMA/EGDM | 80/20 | IPA | 66.7 | 44.4 | 78.3 | 44.4 |

TABLE XVII

| Monomers | Mole Ratio | Solvent | Adsorption Capacity % | | | |
|---|---|---|---|---|---|---|
| | | | Water | PEG | Glycerine | EHO |
| HEMA/EGDM | 20/80 | IPA | 54.5 | 54.5 | 54.5 | 50 |
| HEMA/EGDM | 30/70 | IPA | 58.3 | 64.3 | 58.3 | 54.5 |
| HEMA/EGDM | 40/60 | IPA | 58.3 | 61.5 | 64.3 | 54.5 |
| HEMA/EGDM | 50/50 | IPA | 61.5 | 61.5 | 61.5 | 50 |
| HEMA/EGDM | 60/40 | IPA | 61.5 | 64.3 | 61.5 | 50 |
| HEMA/EGDM | 70/30 | IPA | 58.3 | 64.3 | 58.3 | 50 |
| HEMA/EGDM | 80/20 | IPA | 61.5 | 58.3 | 61.5 | 54.5 |

In FIG. 11, there will be seen the hourglass 10 of the fragrance release device of the present invention including a frame structure 30 which houses the chambers 13 and 14 of the hourglass 10, and maintains the chambers in an upright orientation. The frame 30 is removably associated with the hourglass 10, and other than orienting the hourglass, performs a decorative function. Frame 30 has a top plate 40, a lower plate 41, and three rods 42, fixed in lower plate 41 but releaseably associated with the top plate 40 by bolts 43. Hourglass 10 includes a porous particulate carrier 16 shown flowing from chamber 13 into chamber 14. As noted previously, the carrier 16 is a polymethacrylate powder or bead, and the carrier includes a suitable fragrance material entrapped therein and uniformly distributed therethrough.

The details of the hourglass 10 can be seen in FIG. 12 in which the hourglass will be seen to include a top surface 11 and a bottom surface 12. Chamber 13 is formed of an air impermeable material 18, while chamber 14 is constructed of an air permeable material. In either case, it is preferred that the chambers 13 and 14 each be fabricated from a clear material in order that the consumer may view the contents of the hourglass as the carrier 16 moves from chamber to chamber. Between the two chambers 13 and 14 is the restricted channel 15 having flow passageway 19 therein for accommodating the passage of the porous particulate carrier 16 between the chambers 13 and 14. A stopcock 20 or a valve is arranged in the channel 15 in order that the particle flow between the chambers can be controlled. Prior to use of the device, the flow controller 20 is maintained closed in order that the carrier 16 is maintained in the chamber 13. The controller 20 is opened when the consumer desires to utilize the device in its fragrance release mode at which time the carrier begins to flow into chamber 14. Because of the air permeable nature of material 17, the fragrance entrapped in the carrier 16 is released into the environment. The carrier can be allowed to remain in chamber 14 for subsequent release of the fragrance, or the hourglass 10 can be inverted at which time the carrier will flow back into chamber 13. Closing of flow controller 20 will thereupon cease the fragrance release function and cause the carrier to be maintained in chamber 13 along with the fragrance because of the air impermeable material 18 used to construct chamber 13.

Two alternate embodiments of the invention are shown in FIGS. 13-14. In FIG. 13, the channel 15 is formed of two sections which can be mated one with the other. Thus, channel 15 includes a threaded shaft 24 which is a continuation of the channel 15 extending from chamber 13. Threaded bore 25 is an extension of channel 15 which continues to chamber 14. In place of valve 20, there is employed a removable insert 26 having a tab 27 which the consumer grasps to remove the insert. The insert 26 is used to prevent the carrier 16 in chamber 13 from flowing into the chamber 14 during shipment and storage of the device. Once the consumer decides to employ the device, it is simply required to separate the two chambers 13 and 14 at the joint formed by the shaft 24 and bore 25, remove the insert 26 by grasping the tab 27, and re-assembling the two halves 13 and 14 of the hourglass 10.

FIG. 14 is similar to FIG. 12 except that the valve 20 of FIG. 12 has been replaced with a removable plug 21 having a ring 22 which is utilized in order to remove the plug 21 from the passageway 19 of channel 15. In FIG. 14, the consumer unscrews the screw threaded closure 23 and grasps the ring 22 removing the plug 21, and replaces the closure 23. The embodiment of FIG. 12 possesses the advantage that the flow of the carrier can be controlled during use with the valve 20, while in the embodiments of FIGS. 13-14, the flow cannot be controlled once the insert 26 and the plug 21 have been removed.

As noted previously, the material 18 of chamber 13 is air impermeable, whereas the material 17 of chamber 14 is air permeable. Suitable air impermeable materials include but are not limited to glass, acrylic polymers, polycarbonate plastics, and sulfone polymers. These same materials can be used for the air permeable material by providing openings in the surface of chamber 14. Otherwise, a more suitable material for the air permeable chamber 14 is a silicone resin or elastomer. If sufficiently air permeable, there can also be employed woven fiber glass or fiber glass reinforced plastics. The silicone resins are preferred however.

The device may include any type of fragrance, cologne, or perfume. For example, the fragrance may be a natural product such as Ambergris, Benzoin, Civet, Clove Leaf Oil, Galbanum, Jasmine Absolute, Labdanum, Mate', Melilot, Mimosa, Musk Tonquin, Myrrh, Mousse de Chene, Olibanum, Opopanax, Orris, Patchouli, Rosemary Oil, Sandalwood Oil, Vetivert Oil, and Violet Leaves Absolute. Among the various aroma chemicals that may be employed in addition to the foregoing natural products are, for example, acetylated cedarwood terpenes, amylcinnamic aldehyde, amyl salicylate, methyl salicylate, benzyl acetate, benzyl salicylate, p-tert-butylcyclohexyl acetate, citronellol, coumarin, Galaxolide, geraniol, hexylcinnamic aldehyde, isobornyl acetate, linalool, linalyl acetate, Lyral, musk ambrette, phenethyl alcohol, tetrahydromuguol, and terpinyl acetate. Fragrances that have become classics as descriptors for other fragrances in the same family are also included herein and would comprehend the Straight Floral Family, Floral Bouquet Family, Aldehydic Floral Family, Oriental Family, Chypre Family, Woody Family, Green Family, Citrus Family, Fougere Family, Canoe Family, Musk Family, Animal Family, Leather Family, Spice Family, and the Herbal Family.

Active fragrances, perfumes or colognes, may be co-formulated with aqueous or oil type liquid excipients including those excipients which are suitable for modifying release rates. Excipients are employed to increase the solubility of active fragrances in a matrix and thereby result in an increase in the release of fragrances from the device. Such excipients may consist of but are not limited to glycerol, propylene glycol, polyethylene glycol, mineral oil, coconut oil, isopropyl palmitate, isopropyl myristate, and various silicone fluids. Fragrance devices can be prepared containing the fragrance oils Citronellal, Cineole, YSL PARIS ®, manufactured by Charles of the Ritz Group of New York, NY, JOY ®, manufactured by Jean Patou, Inc. of New York, NY; OSCAR de la RENTA ®, manufactured by Oscar de la Renta, Ltd. of New York, NY; and IVOIRE de BALMAIN ™, manufactured by Balmain International B. V. of Rotterdam Netherlands. The fragrance devices possess the characteristic organoleptic properties of each respective fragrance which is noticeable after fabrication and lasts for several weeks.

Table XVIII shows various other fragrance type materials that can be entrapped in accordance with the procedure of Example II. Example III can also be employed to produce fragrance entrapped beads.

TABLE XVIII

| Compound | % Entrapped | Monomers | Mol Ratio |
|---|---|---|---|
| Methyl Anthranilate | 10–50 | LM 0.2 | TETRA 0.8 |
| Dimethyl Anthranilate | 10–50 | LM 0.2 | TETRA 0.8 |
| Indole | 10–50 | LM 0.2 | TETRA 0.8 |
| Geranyl Acetate | 20–80 | LM 0.2–0.8 | EG 0.8-0.2 |
| Benzyl Acetate | 20–80 | LM 0.2–0.8 | EG 0.8-0.2 |
| Anthracine 08 | 10–50 | LM 0.2 | TETRA 0.8 |
| Dihydro Myrcenol | 10–50 | LM 0.2 | TETRA 0.8 |
| Linallyl Acetate | 10–60 | LM 0.2 | TETRA 0.8 |
| Phenyl Ethyl Alcohol | 10–80 | LM 0.2 | TETRA 0.8 |
| Methyl Cinnamate | 10–70 | LM 0.2 | TETRA 0.8 |
| Terpineol | 10–60 | LM 0.2 | TETRA 0.8 |
| Diethyl Phtalate | 10–70 | LM 0.2 | TETRA 0.8 |

TABLE XVIII-continued

| Compound | % Entrapped | Monomers | Mol Ratio |
|---|---|---|---|
| Benzyl Salicylate | 10–60 | LM 0.2 | TETRA 0.8 |

TABLE XIX

| Compound | % Entrapped | Monomers | Mol Ratio |
|---|---|---|---|
| n-Methoxybenzaldehyde (AUBEPINE) | 10–80 | LM 0.2–0.8 | EG 0.2–0.8 |
| n-Cyano-Methoxyphenol Aubepine Nitrile | 10–80 | LM 0.2–0.8 | EG 0.2–0.8 |
| Eugenol | 10–50 | LM 0.2 | TETRA 0.8 |
| Isoeugenol | 10–50 | LM 0.2 | TETRA 0.8 |
| Methoxy 4 Methyl Phenol-2 | 10–50 | LM 0.2 | TETRA 0.8 |
| Fir Needle Oil Siberian | 10–50 | LM 0.2 | TETRA 0.8 |
| Ethyl Safranate (Safran) | 10–50 | LM 0.2 | TETRA 0.8 |
| Thuja Oil | 10–50 | LM 0.2 | TETRA 0.8 |
| Vetiver Oil Boubbon | 10–50 | LM 0.2 | TETRA 0.8 |
| Benzyl Benzoate | 10-60 | LM 0.2 | EG 0.8 |

LM = lauryl methacrylate
EG = ethylene glycol dimethacrylate
TETRA = tetraethylene glycol dimethacrylate It will be apparent from the foregoing that many other variations and modifications may be made in the devices, structures, compounds, compositions, and methods described herein without departing substantially from the essential features and concepts of the present invention. Accordingly, it should be clearly understood that the forms of the invention described herein are exemplary only and are not intended as limitations of the scope of the present invention.

That which is claimed is:

1. A fragrance releasing device comprising a container having at least two chambers, one chamber being constructed of an air impermeable material and the other chamber being constructed of an air permeable material, means forming a channel for providing communication between the two chambers, the channel forming means providing a reduced and restricted passageway between the two chambers, the passageway being of a diameter substantially less than the diameter of the two chambers, porous particulate carrier means in one of said chambers, the size of the passageway being sufficient for allowing passage of the particulate carrier means from one chamber to the other chamber when the container is inverted, the particulate carrier means being in the form of a powder, the powder constituting a combined system of particles, the system of powder particles including unit particles of a size less than about one micron in average diameter, agglomerates of fused unit particles of sizes in the range of about twenty to about eighty microns in averages diameter, and aggregates of clusters of fused agglomerates of sizes in the range of about two hundred to about twelve hundred microns in average diameter, and a fragrance contained and entrapped within the carrier means.

2. The device of claim 1 wherein the shape of each chamber of the container is symmetrical.

3. The device of claim 2 wherein the container is formed in the shape of an hourglass.

4. The device of claim 1 wherein the powder is formed of a highly cross-linked polymethacrylate copolymer.

5. The device of claim 4 including blocking means arranged in said passageway for preventing movement of the particulate carrier means from one chamber of the container to the other chamber of the container.

6. The device of claim 5 wherein the two chambers of the container are formed of a transparent material in order that the contents of the chambers are rendered visible.

* * * * *